United States Patent
Ohkubo

(10) Patent No.: US 12,414,940 B2
(45) Date of Patent: Sep. 16, 2025

(54) METHOD OF TREATING MALIGNANT TUMOR BY AZABICYCLIC COMPOUND

(71) Applicant: TAIHO PHARMACEUTICAL CO., LTD., Chiyoda-ku (JP)

(72) Inventor: Shuichi Ohkubo, Tsukuba (JP)

(73) Assignee: TAIHO PHARMACEUTICAL CO., LTD., Chiyoda-ku (JP)

( * ) Notice: Subject to any disclaimer, the term of this patent is extended or adjusted under 35 U.S.C. 154(b) by 794 days.

(21) Appl. No.: 17/055,446

(22) PCT Filed: May 14, 2019

(86) PCT No.: PCT/JP2019/019010
§ 371 (c)(1),
(2) Date: Nov. 13, 2020

(87) PCT Pub. No.: WO2019/221086
PCT Pub. Date: Nov. 21, 2019

(65) Prior Publication Data
US 2021/0177813 A1   Jun. 17, 2021

(30) Foreign Application Priority Data
May 14, 2018   (WO) .................. PCT/JP2018/018593

(51) Int. Cl.
  *A61K 31/437*   (2006.01)
  *A61K 9/00*   (2006.01)
  *A61P 35/00*   (2006.01)
(52) U.S. Cl.
  CPC .......... *A61K 31/437* (2013.01); *A61K 9/0053* (2013.01); *A61P 35/00* (2018.01)
(58) Field of Classification Search
  None
  See application file for complete search history.

(56) References Cited

U.S. PATENT DOCUMENTS

2012/0108589 A1   5/2012   Kitade et al.

FOREIGN PATENT DOCUMENTS

| JP | 2006-306775 A | 11/2006 |
| WO | WO 2011/004610 A1 | 1/2011 |

OTHER PUBLICATIONS

International Search Report issued on Jun. 18, 2019 in PCT/JP2019/019010 filed on May 14, 2019, 2 pages.
Whitesell et al., "HSP90 and the Chaperoning of Cancer", Nature Reviews | Cancer, 2005, vol. 5, pp. 761-772.
Kamal et al., "Therapeutic and diagnostic implications of Hsp90 activation", Trends in Molecular Medicine, 2004, vol. 10, No. 6, pp. 283-290.
Banerji, "Heat Shock Protein 90 as a Drug Target: Some Like It Hot", Molecular Pathways, Clin. Cancer Res., 2009, vol. 15, No. 1, pp. 9-14 (7 total pages).
Taldone et al., "Targeting Hsp90: small-molecule inhibitors and their clinical development", Current Opinion in Pharmacology, 2008, vol. 8, pp. 370-374.
Li et al., "New developments in Hsp90 inhibitors as anti-cancer therapeutics: Mechanisms, clinical perspective and more potential", Drug Resistance Updates, 2009, vol. 12, pp. 17-27.
Ohkubo et al., "TAS-116, a Highly Selective Inhibitor of Heat Shock Protein 90α and β, Demonstrates Potent Antitumor Activity and Minimal Ocular Toxicity in Preclinical Models", Molecular Cancer Therapeutics, 2015, vol. 14, No. 1, pp. 14-22 (15 total pages).
Renouf et al., "Ocular Toxicity of Targeted Therapies", Journal of Clinical Oncology, 2012, vol. 30, No. 26, pp. 3277-3286.
Suzuki et al., "TAS-116 Second-generation HSP90-α/β inhibitor Cancer therapy", Drugs of the Future, 2018, vol. 43, No. 1, pp. 13-21 (11 total pages).
JapicCTI-163182, [online], [retrieved on Jul. 18, 2018], retrieved from the Internet: URL:http://www.clinicaltrials.jp/user/cteSearch.jsp, (Japan Pharmaceutical Information Center, JAPIC Clinical Trials Information, 2017, 6 total pages.
Yanagitani et al., "First-in-human phase I study of an oral HSP90 inhibitor, TAS-116, in advanced solid tumors.", ASCO Meeting Library, [online], [retrieved on Jul. 10, 2018], retrieved from the Internet: URL:https://meetinglibrary.asco.org/record/149483/abstract, Presented Monday, Jun. 5, 2017, 1 page.
Kurokawa et al., "Phase II study of TAS-116, an oral inhibitor of heat shock protein 90 (HSP90), in metastatic or unresectable gastrointestinal stromal tumor refractory to imantinib, sunitinib and regorafenib", Annals of Oncology, 2017, vol. 28, Suppl. 5, pp. 522-523 (2 total pages).
Shimomura et al., "Abstract B87: First-in-human Phase I dose escalation study of TAS-116, a novel, orally active HSP90α and HSP90⊕ selective inhibitor, in patients with advanced solid tumors", [abstract], Proceedings of the AACR-NCI-EORTC International Conference: Molecular Targets and Cancer Therapeutics; 2015, vol. 14, Issue 12, Suppl. 2, 5 total pages.

(Continued)

*Primary Examiner* — Dale R Miller
(74) *Attorney, Agent, or Firm* — Oblon, McClelland, Maier &Neustadt, L.L.P.

(57) ABSTRACT

Provided is a method of treating malignant tumor by an azabicyclic compound, particularly, with eye disorder reduced. The present invention provides a method for treating malignant tumor, comprising administering an effective amount of 3-ethyl-4-[3-(1-methylethyl)-4-[4-(1-methyl-1H-pyrazol-4-yl)-1H-imidazol-1-yl]-1H-pyrazolo[3,4-b]pyridin-1-yl]benzamide (compound 1) or a salt thereof to a patient in need thereof according to a dosing regimen, wherein the dosing regimen comprises administering the compound 1 or the salt thereof at a dose from 40 mg/body/day to 240 mg/body/day in terms of the amount of the compound 1 for consecutive days, and then providing a withdrawal period of at least 2 days.

26 Claims, 2 Drawing Sheets

(56) References Cited

OTHER PUBLICATIONS

Taiho Oncology, Inc., Archive history for NCT02965885, ClinicalTrials.gov archive, U.S. National Library of Medicine, [online], [retrieved on Jul. 10, 2018], retrieved from the Internet: URL:https://clinicaltrials.gov/ct2/history/NCT02965885?A=1&B=1&C=merged, 2016, 6 total pages.
Yong et al., "Phase I study of KW-2478, a novel Hsp90 inhibitor, in patients with B-cell malignancies", British Journal of Cancer, 2016, vol. 114, pp. 7-13.
Yanagitani et al., "First-in-human phase I study of an oral HSP90 inhibitor, TAS-116, in advanced solid tumors.", ASCO Meeting Library, [poster], 2017, 1 page.
Yanagitani et al., "First-in-human phase I study of an oral HSP90 inhibitor, TAS-116, in advanced solid tumors.", Abstract #186280, Jun. 5, 2017, 1 page.
Kurokawa et al., "Phase II study of TAS-116, an oral inhibitor of heat shock protein 90 (HSP90), in metastatic or unresectable gastrointestinal stromal tumor refractory to imatinib, sunitinib and regorafenib", Annals of Oncology, [poster], 2017, 1 page.
Kurokawa et al., "Phase II study of TAS-116, an oral inhibitor of heat shock protein 90 (HSP90), in metastatic or unresectable gastrointestinal stromal tumor refractory to imatinib, sunitinib and regorafenib", Abstract 1811, Clinical trial JapicCTI-163182, 2017, 1 page.
ESMO Congress in partnership with European Association for Cancer Research (EACR), Madrid, Spain, Sep. 11, 2017, 326 pages.
"A phase 2 study of TAS-116 in patients with GIST" Mar. 3, 2016; Trial ID CT2080223127; JapicCTI-163182 URL: https://jrct.niph.go.jp/pages/en-detail/54738/jRCT/3 (3 pages).
Hitotsumachi et al., "TAS-116, an Orally Highly Potent HSP90 α/β Selective Inhibitor, Leads Minimized Ocular Toxicity in Both Albino and Pigmented Rats"; Society of Toxicology Annual Meeting 2013 (poster; #1811) (1 page).
Hitotsumachi et al., "TAS-116, an orally highly potent HSP90α/β selective inhibitor, leads minimized ocular toxicity' in both albino and pigmented rats"; Society of Toxicology Annual Meeting 2013 (English abstract; ID: 1537168) (1 page).
Hitotsumachi et al.. "Heat shock protein 90 inhibitor, TAS-116. demonstrates favorable tissue distribution'profiles and leads to minimized ocular toxicity"; European Societies of Toxicology (EUROTOX) 2013 (poster; #P23-09) (1 page).
Hitotsumachi et al., Heat Shock Protein 90 inhibitor, TAS-116, demonstrates favorable tissue distribution profiles and leads to minimized ocular toxicity'; European Societies of Toxicology (EUROTOX) 2013 (English abstract) (1 page).
Kodama et al., "Discovery of a Novel Oral HSP90 Inhibitor, TAS-116-Antitumor Effects Due to High Tumor Translocation and Avoidance of Ocular Toxicity"; Japanese Association for Molecular Target Therapy of Cancer 2013 (poster) (1 page).
Kodama et al., "Discovery of a Novel Oral HSP90 Inhibitor, TAS-116-Antitumor Effects Due to High Tumor Translocation and Avoidance of Ocular Toxicity"; Japanese Association for Molecular Target Therapy of Cancer 2013 (machine translation) (1 page).
Yoshimura et al., Evolution of highly selective HSP90 α/β inhibitors with unique binding mode;; 24th EORTC—NCI—AACR Symposium on Molecular Targets and Cancer Therapeutics 2012 (poster; #292) (1 page).
Kodama et al., "TAS-116, a novel, orally bioavailable highly potent HSP90α/β selective inhibitor demonstrates favorable tissue distribution properties which lead to minimized ocular toxicity"; 24th EORTC—NCI—AACR Symposium on Molecular Targets and Cancer Therapeutics 2012 (poster; #491) (1 page).
Ohkubo et al., TAS-116, a novel, orally bioavailable HSP90α/β selective inhibitor demonstrates highly potent antitumor activity in preclinical models with a favorable PK profile; 24th EORTC—NCI—AACR Symposium on Molecular Targets and Cancer Therapeutics 2012 (poster; #492) (1 page).
Suzuki et al., "Anti-tumor activities of selective HSP90α/β inhibitor, TAS-116, in combination with bortezomib in multiple myelomaleukemia" Leukemia. Feb. 2015;29(2):510-4, 30 pages.

Suzuki et al.,"Combination treatment of HSP90 α / β inhibitor and RAS-RAF-MEK-ERK inhibitor for myeloma treatment" International Journal of Myeloma 2015. 5(2) O-60, 8 pages.
Suzuki et al., "Combination of a Selective HSP90α/β Inhibitor and a RAS-RAF-MEK-ERK Signaling Pathway Inhibitor Triggers Synergistic Cytotoxicity in Multiple Myeloma Cells" PLoS One. Dec. 2, 2015;10(12), 20 pages.
Shimomura et al., "FIH Ph1 dose-escalation study of TAS-116, a novel, orally active HSP90 α/β selective inhibitor, in patients with advanced solid tumors" [poster]AACR-NCI-EORTC 2015_#B87, 2 pages.
Shimomura et al., "FIH Ph1 dose-escalation study of TAS-116, a novel, orally active HSP90 α/β selective inhibitor, in patients with advanced solid tumors" [abstract]AACR-NCI-EORTC 2015_#B87, 1 page.
Ohkubo et al., "The discovery and development of oral HSP90α/β inhibitor, TAS-116"Molecular Chaperones in Cancer Madrid,[slides] session#5 p. 65 May 4, 2017.
Ohkubo et al., "The discovery and development of oral HSP90a/B inhibitor, TAS-116"Molecular Chaperones in Cancer Madrid, [abstract] session#5 p. 65 May 4, 2017, 136 pages.
Saito et al., "TAS-116 inhibits oncogenic KIT signalling on the Golgi in both imatinib-naïve and imatinib-resistant gastrointestinal stromal tumours" Br J Cancer. Mar. 2020; 122(5):658-667.
Joseph W. Jackson, et al., "Pharmacologic dissection of the overlapping impact of heat shock protein family members on platelet function" J Thromb Haemost. May 2020;18(5):1197-1209, 13 pages.
Kihara et al., "Pimitespib is effective on cecal GIST in a mouse model of familial GISTs with KIT-Asp820Tyr mutation through KIT signaling inhibition" Experimental and Molecular Pathology 123 (2021) 104692 p. 1-8.
Teranishi et al.,"Combination of pimitespib (TAS-116) with sunitinib is an effective therapy for imatinib-resistant gastrointestinal stromal tumors" Int J Cancer. Jun. 1, 20235;152(12):2580-2593. 14 pages.
Sano et al., "Characterization of cell line with dedifferentiated GIST-like features established from cecal GIST of familial GIST model mice" Pathol Int. May 2023;73(5): pp. 181-187.
Naito et al., "Chapter-GIST-101: A phase I study of pimitespib combined with imatinib in patients with imatinib-refractorygastrointestinal stromal tumor" [abstract]_1917MO S1031_vol.34_Issue S2_ESMO 2023.
Naito et al., "Chapter-GIST-101: A phase I study of pimitespib combined with imatinib in patients with imatinib-refractory gastrointestinal stromal tumor" [slides]_1917MO_ESMO 2023, 10 pages.
Naito et al., "Current status of and future prospects for the treatment of unresectable or metastatic gastrointestinal stromal tumours" Gastric Cancer.May 2023;26(3):339-351(13 pages).
Doi et al., "Pimitespib for the treatment of advanced gastrointestinal stromal tumors and other tumors" Future Oncol. Mar. 2024;20(9):507-519, 13 pages.
Shibata et al.,"Utility of Cryopreserved Hepatocytes Suspended in Serum to Predict Hepatic Clearance in Dogs and Monkeys" Drug Metab Pharmacokinet. 2014;29(2):168-76, 9 pages.
Kawazoe et al.,"TAS-116 (Pimitespib), an Oral HSP90 Inhibitor, in Combination with Nivolumab in Patients with Colorectal Cancer and Other Solid Tumors: An Open-Label, Dose-Finding, and Expansion Phase Ib Trial (EPOC1704)" Clin Cancer Res. Dec. 1, 20215;27(24): pp. 6709-6715, 7 pages.
Takei et al.,"Multiomic molecular characterization of the response to combination immunotherapy in MSS/pMMR metastatic colorectal cancer" J Immunother Cancer. Feb. 8, 2024;12(2):e008210, 21 pages.
Doi et al.,"Pimitespib pooled safety profile analysis in patients with solid tumors, including gastrointestinal stromal tumor"[abstract] FR1-1_JSCO2023 Oct. 19, 2023. 1 page.
Doi et al.,"Pimitespib pooled safety profile analysis in patients with solid tumors, including gastrointestinal stromal tumor"[slides] FR1-1_JSCO2023 Oct. 19, 2023, 12 pages.
Komatsu et al.,"An open-label, crossover study to compare different formulations and evaluate effect of food on pharmacokinetics of pimitespib in patients with advanced solid tumors" Investigational New Drugs Published: Aug. 6, 2022 Volume 40, pp. 1011-1020, (2022).

(56) References Cited

OTHER PUBLICATIONS

Kurokawa et al., "Pimitespib, an oral inhibitor of heat shock protein 90 in advanced gastrointestinal stromal tumor refractory to standard therapy:Results from the expanded access program"[abstract]FR1-7 JSCO2023 Oct. 19, 2023.

Kurokawa et al., "Pimitespib, an oral inhibitor of heat shock protein 90 in advanced gastrointestinal stromal tumor refractory to standard therapy:Results from the expanded access program"[slides]FR1-7 JSCO2023 Oct. 19, 2023, 18 pages.

Kasahara et al.,"A Phase 1 Study to Compare Formulations and Evaluate the Effect of Food on Pimitespib in Patients with Solid Tumors"[slides] M025-5 JSMO2022 Feb. 18, 2022, 12 pages.

Sawaki et al.,"A phase III trial of pimitespib (TAS-116) in patients with advanced gastrointestinal stromal tumor: Chapter-GIST-301" [abstract] #10546 PS4-3 JSMO2022 Feb. 19, 2022, 2 pages.

Sawaki et al.," phase III trial of pimitespib (TAS-116) in patients with advanced gastrointestinal stromal tumor Chapter-GIST-301" [slides] PS4-3 JSMO2022 Feb. 19, 2022, 29 pages.

Hirano et al., " Chapter-GIST-101: A phase I study of pimitespib combined with imatinib in patients with imatinib-refractory gastrointestinal stromal tumor." TPS97 ASCO Journal of Clinical Oncology vol. 42, No. 23_suppl, 1 page.

Ikebe et al., TAS-116 pimitespib a heat shock protein 90 inhibitor shows efficacy in preclinical. Cancer Science 2022;113 684-696.

Shimizu et al., "PBPK Modeling Using Simcypto Evaluate Drug-Drug Interaction Potential of Pimitespib" Otsuka Simcyp User Forum Dec. 15, 2022, 35 pages.

Uno et al., "TAS-116 , an orally available HSP90αβ selective inhibitor-Synthesis and biological evaluation-" Abstract C127 AACR-NCI-EORTC Nov. 1, 2013, 5 pages.

Uno et al., "TAS-116 orally available HSP90αβ selective inhibitor-Synthesis and biological evaluation-" {slides] C127 AACR-NCI-EORTC Nov. 1, 2013, 1 page.

Uno et al., 'Discovery of 3-Ethyl-4-(3-isopropyl-4-(4-(1-methyl-1H-pyrazol-4-yl)-1H-imidazol-1-yl)-1H-pyrazolo[3,4-b]pyridin-1-yl)benzamide(TAS-116) as a Potent, Selective, and Orally Available HSP90 Inhibitor', J. Med.Chem 2019, 62, 531-551.

Muraoka et al., "TAS-116, an orally available HSP90α/β selective inhibitor, has potent antitumor activity in small cell lung cancer as a single agent and in combination with an anthracycline derivative, amrubicin."[Abstract] C128 vol. 12, Issue 11_Supplement Nov. 1, 2013 AACR-NCI-EORTC, 5 pages.

Muraoka et al., "TAS-116, an orally available HSP90α/β selective inhibitor, has potent antitumor activity in small cell lung cancer as a single agent and in combination with an anthracycline derivative, amrubicin."[Poster] 2013 AACR-NCI-EORTC, 1 page.

Muraoka et al., "TAS-116, an orally available HSP90α/β selective inhibitor, exhibits synergistic effects in combination with taxanes in EGFR-tyrosine kinase inhibitor-resistant human NSCLC xenograft models through the downregulation of key molecules involved in drug resistance of cancer chemotherapy. "[Abstract] C129 vol. 12, Issue 11_Supplement Nov. 1, 2013 AACR-NCI-EORTC, 5 pages.

Muraoka et al., "TAS-116, an orally available HSP90α and β selective inhibitor, exhibits synergistic effects in combination. with taxanes in EGFR-tyrosine kinase inhibitor-resistant human NSCLC xenograft models through the downregulation of key molecules involved in drug resistance of cancer chemotherapy."[Poster] vol. 12, Issue 11_Supplement Nov. 1, 2013 AACR-NCI-EORTC. 1 page.

Yoshimura et al., 'Thermodynamic Dissection of Potency and Selectivity of Cytosolic Hsp90 Inhibitors' J. Med. Chem. 2021, 64, 2669-2677, 9 pages.

Uno et al., 'Discovery of TAS-116, a novel oral HSP 90 inhibitor' 37th Symposium on Medicinal Chemistry Medchem News 30(3) 133-136 (2020) with machine translation.

Uno et al., 'Discovery of TAS-116, a novel oral HSP 90 inhibitor' 37th Symposium on Medicinal Chemistry Medchem News 30(3) 133-136 (2020.

Okihira et al., 'In vitro study about the absorption of weakly basic drugs in cancer patients' [2-6] Absorption and distribution 5 2-6-11 The 38th Annual Meeting of the Pharmaceutical Society of Japan May 17, 2023, 28 pages.

Okihira et al., 'In vitro study about the absorption of weakly basic drugs in cancer patients' [2-6] Absorption and distribution 5 2-6-11 The 38th Annual Meeting of the Pharmaceutical Society of Japan May 17, 2023(with machine translation), 28 pages.

Uno et al., 'Discovery of a Novel Oral HSP90 Inhibitor, Pimitespib (TAS-116)'[slides] The 33rd New Drug Discussion Meeting Sep. 5, 2023, 38 pages.

Uno et al., 'Discovery of a Novel Oral HSP90 Inhibitor, Pimitespib (TAS-116)' {slides] The 33rd New Drug Discussion Meeting Sep. 5, 2023(with machine translation), 38 pages.

Uno et al., 'Discovery of a Novel Oral HSP90 Inhibitor, Pimitespib (TAS-116)'[agenda] The 33rd New Drug Discussion Meeting Sep. 5, 2023(with machine translation), 2 pages.

Kawazoe et al.,"TAS-116, an Oral HSP90 Inhibitor, in combination with nivolumab in patients with colorectal cancer and other solid tumors: an open-label, dose-finding, and expansion phase 1b trial(EPOC1704)" [abstract] No. 4044 ASCO 2020, 3 pages.

Kawazoe et al., TAS-116, an Oral HSP90 Inhibitor, in combination with nivolumab in patients with colorectal cancer and other solid tumors: an open-label, dose-finding, and expansion phase 1b trial(EPOC1704) [poster] No. 4044 ASCO 2020., 1 page.

Chong, K.T et al., 'Crystal structure of Hsp90-alpha N-terminal domain in complex with 2-(4-Hydroxy-cyclohexylamino)-4-[5-(4-phenyl-imidazol-1-yl)-isoquinolin-1-yl]-benzamide' FullwwPDB X-ray Structure Validation Report_3wq9_RCSB PDB_Jan 23, 2014, 14 pages.

Yoshimura et al., "Accelerating Drug Discovery with Thermodynamics" Life Science Day 2013 Lecture(1)_July 3, 2013, 20 pages.

Yoshimura et al., "Accelerating Drug Discovery with Thermodynamics" Life Science Day 2013 Lecture(1)_July 3, 20133(with machine translation), 20 pages.

Uno et al.,'Discovery of TAS-116, a novel oral HSP 90 inhibitor' 37th Symposium on Medicinal Chemistry_lecture summary (Sep. 27, 2019), 1 page.

Uno et al.,'Discovery of TAS-116, a novel oral HSP 90 inhibitor' 37th Symposium on Medicinal Chemistry_lecture summary (Sep. 27, 2019) (machine translation), 1 page.

Suzuki et al., 'Antitumor activities of an oral selective HSP90a/b inhibitor, TAS-116, in combination with bortezomib in multiple myeloma'Leukemia. Feb. 2, 20159(2): 510-514. doi:10.1038/leu.2014.300.

Ohkubo et al.,"Drug Discovery of HSP90 Inhibitor pimitespib and Approach to Resistant Cancer" T h e 1st Tokyo University of Science Symposium on Integrative Research of Cancer, Immunology and Mathematics Dec. 2, 2023, 26 pages.

Ohkubo et al., "Drug Discovery of HSP90 Inhibitor pimitespib and Approach to Resistant Cancer" T h e 1st Tokyo University of Science Symposium on Integrative Research of Cancer, Immunology and Mathematics Dec. 2, 2023(machine translation), 33 pages.

Takahashi et al.,"Final analysis of phase III trial of pimitespib (TAS-116) in patients with advanced GIST:Chapter GIST 301" [abstract]O14-4 JSMO2023 Mar. 18, 2023, 4 pages.

Takahashi et al., "Final analysis of phase III trial of pimitespib (TAS-116) in patients with advanced GIST:Chapter GIST 301" [slides]JSMO2023 O14-4 JSMO2023 Mar. 18, 2023, 14 pages.

Shimomura et al., "The efficacy and safety of pimitespib in patients with solid tumors: A phase 1 study to assess cardiac safety" [abstract] 07-3 JSMO2024_Feb 22, 2024, 5 pages.

Shimomura_ et al., "The efficacy and safety of pimitespib in patients with solid tumors:a phase 1 study to assess cardiac safety"[slide] 07-3 JSMO2024_Feb 22, 2024, 14 pages.

Karayama et al., "Cardiovascular Safety of Pimitespib in Patients with Solid Tumors: A Phase 1 Study" MO14-2 JSMO2023_Mar16, 2023, 13 pages.

Naito et al., "Pimitespib in patients with advanced gastrointestinal stromal tumors in Japan: an expanded access program" International Journal of Clinical Oncology, Feb. 2, 20258. doi: 10.1007/s10147-025-02726-0.

(56) References Cited

OTHER PUBLICATIONS

Tsuge et al., "The HSP90 Inhibitor Pimitespib Targets Regulatory T Cells in the Tumor Microenvironment" Cancer Immunology Research, Feb. 3, 2025;13(2):273-285. doi: 10.1158/2326-6066.CIR-24-0713.
Doi et al., "Pimitespib for the treatment of advanced gastrointestinal stromal tumors and other tumors" Future Oncology, 20(9):507-519, Dec. 5, 2023 (Infographic attached) 15 pages.
Naoki et al., "Cardiovascular safety of pimitespib in patients with advanced solid tumors: An open-label, nonrandomized, phase 1 study" Cancer; 130(21):3745-3756. doi: 10.1002/cncr.35447. Nov. 1, 2024(Epub Jul. 10, 2024).
Matsubara et al., "Chapter-Platform-201: Phase 2 trial of pimitespib plus enzalutamide for patients with metastatic castration-resistant prostate cancer." [Poster Bd M15]; 2025 ASCO Genitourinary Cancers Symposium, Feburary 13, 2025(program guide attached).
Matsubara et al., "Chapter-Platform-201: Phase 2 trial of pimitespib plus enzalutamide for patients with metastatic castration-resistant prostate cancer."; [Abstract TPS296] ; 2025 ASCO Genitourinary Cancers Symposium, Feburary 18, 2025.
Nakajima et al., "A Phase 1 Study of PARP inhibitor (Niraparib) plus HSP90 inhibitor (Pimitespib) in Solid Tumors: The NiraPim (EPOC2102) Study" [Poster 683TIP] ESMO Congress 2024, Sep. 14, 2024, 1 page.
Nakajima et al., "A Phase 1 Study of PARP inhibitor (Niraparib) plus HSP90 inhibitor (Pimitespib) in Solid Tumors: The NiraPim (EPOC2102) Study" [Abstract] ESMO Congress 2024, Sep. 14, 2024,1 page.
Naito et al., "Treatment Patterns in Patients with Advanced Gastrointestinal Stromal Tumor in Japan: An Administrative Claims Database Study" [Slides: MO26-5] 22nd Japanese Society of Medical Oncology Annual Meeting, Mar. 7, 2025 (attached program with machine translation), 19 pages.
Naito et al., "Treatment Patterns in Patients with Advanced Gastrointestinal Stromal Tumor in Japan: An Administrative Claims Database Study" [Abstract: MO26-5] 22nd Japanese Society of Medical Oncology Annual Meeting, Mar. 7, 2025, 6 pages.
Komatsu et al., "Treatment Patterns in Patients with Advanced Gastrointestinal Stromal Tumor in Japan: An Administrative Claims Database Study" [Poster Bd J2] 2025 ASCO Gastrointestinal Cancers Symposium, Jan. 23, 2025(program guide attached), 4 pages.
Komatsu et al., "Treatment Patterns in Patients with Advanced Gastrointestinal Stromal Tumor in Japan: An Administrative Claims Database Study" [Abstract 811] 2025 ASCO Gastrointestinal Cancers Symposium, Jan. 27, 2025, 3 pages.
Yong et al., "Chapter-GIST-101: A phase I study of pimitespib combined with imatinib in patients with imatinib-refractory gastrointestinal stromal tumor" [Poster 267TIP] ESMO Asia Congress 2024, Dec. 7, 2024, 1 page.
Yong et al., "Chapter-GIST-101: A phase I study of pimitespib combined with imatinib in patients with imatinib-refractory gastrointestinal stromal tumor" [Abstract] ESMO Asia Congress 2024, Dec. 7, 2024, 1 page.
Zalcberg, "Chapter-GIST-101: A phase I study of pimitespib combined with imatinib in patients with imatinib refractory gastrointestinal stromal tumor" [Poster]; GISTT Summit 2024, Oct. 16-18, 2024, 1 page.
Hirano et al., "Chapter-GIST-101:A phase I study of pimitespib combined with imatinib in patients with imatinib-refractory gastrointestinal stromal tumor" [Poster Bd L6]; 2024 ASCO Breakthrough, Aug. 8, 2024(program guide attached); 4 pages.
Hirano et al., "Chapter-GIST-101:A phase I study of pimitespib combined with imatinib in patients with imatinib-refractory gastrointestinal stromal tumor" [Slides]; 2024 ASCO Breakthrough, Aug. 8, 2024, 5 pages.
Hirano et al., "Chapter-GIST-101:A phase I study of pimitespib combined with imatinib in patients with imatinib-refractory gastrointestinal stromal tumor" [Abstract TPS97]; 2024 ASCO Breakthrough, Aug. 12, 2024; 3 pages.
Nakajima et al., "A Phase 1 Study of PARP Inhibitor (Niraparib) plus HSP90 Inhibitor (Pimitespib) in Solid Tumors: Dose-escalation Results from the NiraPim (EPOC2102) Study" [Slides:FR1-6] JSCO 62nd Annual Meeting, Oct. 24, 2024 (program attached), 18 pages.
Shimomura et al., "The efficacy and safety of pimitespib in patients with solid tumors: a phase 1 study to assess cardiac safety" [Slides:07-3] JSMO2024, Feb. 22, 2024 (program attached), 18 pages.
Okuhira et al., "Differences in dissolution behavior of after pH-shift basic compounds due to change in API manufacturing process" [Slides] The 49th Kansai Physical Properties Research Association, Mar. 31, 2024, With English Machine Translation, 75 pages.
Okuhira et al., "Differences in dissolution behavior of after pH-shift basic compounds due to change in API manufacturing process" [Slides] The 49th Kansai Physical Properties Research Association, May 31, 2024, 4 pages With English Machine Translation.
Ohkubo et al., "TAS-116, a highly selective inhibitor of heat shock protein 90a/B, inhibits tumor growth in biliary tract cancer mouse models" [poster] 26th EORTC-NCI-AACR Nov. 18, 2014, 1 page.
Ohkubo et al., "A multi-pronged, single-agent approach to treating cancers by targeting the molecular chaperone heat shock protein 90" [slides] 73rd JCA Sep. 25, 2014, 18 pages.
Ohkubo et al."Discovery of TAS-116: A Novel Inhibitor of HSP90α and HSP90β"[slides] 13th Discovery on Target Sep. 2015, 29 pages.
Saito et al., "The efficacy of novel HSP90 inhibitor, TAS-116, against gastrointestinal stromal tumors" [abstract] P-1226 Cancer Science vol. 109, Issue S2, p. 432 Dec. 2018 Abstracts of the 77th Annual Meeting of the Japanese Cancer Association Sep. 27, 2018, 1445 pages.
Ohkubo et al., "Discovery and clinical development of TAS-116, a selective HSP90 inhibitor, for the treatment of advanced gastrointestinal stromal tumors" 15th Cancer TR work shop_Jan 17,2020—machine translation-,50 pages,.
Ohkubo et al., "for the treatment of advanced gastrointestinal stromal tumors. Creation of HSP90 inhibitor pimitespib" Symposium on Biological Functionand Drug Discovery Aug. 2, 20235 with Machine English Translation, 54 pages.
Uno et al."novel oral HSP90 inhibitor" Tohoku University Jul. 12, 2019, 218 pages with English Translation.
Uno et al., "Discovery of TAS-116 as a novel orally available HSP90 inhibitor"{Poster:2P-24}37th Medicinal Chemistry Symposium Nov. 27, 2019, 1 page.
Uno et al., "Discovery of TAS-116 as a novel orally available HSP90 inhibitor"{Slide:2P-24}37th Medicinal Chemistry Symposium Nov. 27, 2019, 2 pages.
Uno et al.,, "Creation of TAS-116, a novel oral HSP90 inhibitor"The 141st Pharmaceutical Society of Japan_Mar 27, 2021 with English machine translation, 54 pages.
Ohkubo et al., "Discovery and clinical development of TAS-116, a selective HSP90 inhibitor, for the treatment of advanced gastrointestinal stromal tumors" 15th JAMTTC TR work shop_Jan 17,2020 With English machine translation 77pages.
Emi Ikebe et al., "A highly selective HSP90α/β inhibitor, TAS-116, demonstrates its potent growth suppressive activity to adult T-cell leukemia in preclinical models" Oita University[poster] 18thHTLV Tokyo Mar. 2017, 2 pages.
Uno et al., "Creation of a Novel HSP90 Inhibitor, TAS-116" Kitasato Univ.Nov. 9, 2021 with English machine translation, 150 pages.
Kodama et al., "a novel oral HSP90 inhibitor, TAS-116" Manuscript_ 2013 Molecular Target Therapy of Cancer_Sep 10, 2013 with English machine translation, 4 pages.
Notice of Final Rejection in Korean Application No. 10-2019-0056545, issued Mar. 27, 2024.

METHOD OF TREATING MALIGNANT TUMOR BY AZABICYCLIC COMPOUND

This application is a national stage application of PCT/JP2019/019010, filed on May 14, 2019, which claims priority to PCT/JP2018/018593, filed on May 14, 2018, the contents of which is incorporated herein by reference.

TECHNICAL FIELD

The present invention relates to a method of treating malignant tumor by an azabicyclic compound which has an HSP90 inhibitory effect and exhibits antitumor activity.

BACKGROUND ART

A group of proteins called molecular chaperones have multiple functions in regulating other proteins such as promoting and maintaining the functional structure, promoting correct assembly, inhibiting unnecessary aggregation, protecting against degradation, and promoting secretion (Non-Patent Literature 1). HSP90 is a molecular chaperone present as abundantly as from approximately 1 to 2% of all intracellular soluble proteins, and unlike the other molecular chaperones, is not required for the biosynthesis of a majority of polypeptides (Non-Patent Literature 1). Signal transduction-related factors (e.g., ERBB1/EGFR, ERBB2/HER2, MET, IGF1R, KDR/VEGFR, FLT3, ZAP70, KIT, CHUK/IKK, BRAF, RAF1, SRC, and AKT), cell-cycle regulators (e.g., CDK4, CDK6, Cyclin D, PLK1, and BIRC5), and transcriptional factors (e.g., HIF-1α, p53, androgen receptor, estrogen receptor, and progesterone receptor) are known as major client proteins whose structural formation and stability are controlled through interaction with HSP90 (Non Patent Literatures 2 and 3). HSP90 is deeply involved in cell proliferation and survival by maintaining normal functions of these proteins. Furthermore, mutant or chimeric proteins which cause canceration and exacerbation of cancer (e.g., BCR-ABL and NPM-ALK) require HSP90 for their functions, indicating the importance of HSP90, particularly, for processes such as canceration and survival, proliferation, progression, and metastasis of cancer (Non-Patent Literature 2).

When functions of HSP90 as molecular chaperone are inhibited by its specific inhibitor such as geldanamycin, the inactivation, destabilization, and degradation of client proteins occur, resulting in the arrest of proliferation and apoptosis of cancer cells (Non-Patent Literature 4). From the viewpoint of physiological functions of HSP90, the HSP90 inhibitor is characterized by being able to inhibit multiple signaling pathways involved in the survival and proliferation of cancer at the same time. Therefore, the HSP90 inhibitor is capable of serving as a drug having a wide range of effective anticancer effects. HSP90 derived from cancer cells has higher activity and has higher affinity for ATP or its inhibitor than those of HSP90 derived from normal cells. From this finding, the HSP90 inhibitor is expected as a drug having high cancer selectivity (Non-Patent Literature 5).

The present applicant has reported in Patent Literature 1 that an azabicyclic compound mentioned below has high HSP90 inhibitory activity and antiproliferative effect on cancer cell lines, and is useful as an HSP90 inhibitor.

However, in previous clinical trials of HSP90 inhibitors, the occurrence of eye disorder such as night blindness, photopsia, or blurring of the eyes have often been observed as adverse events, though the degree differs among cases (Non-Patent Literature 7). The toxicity of HSP90 inhibitors to the eyes has also been observed in nonclinical models. Thus, it has been reported that the distribution of an HSP90 inhibitor in the retina correlates with ocular toxicity (Non-Patent Literature 6).

Thus, a method of treating malignant tumor using an HSP90 inhibitor which exhibits an excellent antitumor effect but exhibits no ocular toxicity is needed.

CITATION LIST

Patent Literature

Patent Literature 1: International Publication No. WO 2011/004610

Non-Patent Literature

Non-Patent Literature 1: Nat. Rev. Cancer, 5: 761-772 (2005)
Non-Patent Literature 2: TRENDS Mol. Med., 10: 283-290 (2004)
Non-Patent Literature 3: Clin. Cancer Res., 15: 9-14 (2009)
Non-Patent Literature 4: Curr. Opin. Pharmacol., 8: 370-374 (2008)
Non-Patent Literature 5: Drug Resist. Updat., 12: 17-27 (2009)
Non-Patent Literature 6: Mol. Cancer Ther., 14 (1), 14-22 (2015)
Non-Patent Literature 7: J. Clin. Oncol., 30 (26), 3277-3286 (2012)

SUMMARY OF THE INVENTION

Technical Problem

An object of the present invention is to provide a method of treating malignant tumor by an azabicyclic compound, particularly, with eye disorder reduced.

Solution to Problem

The present inventor had conducted diligent studies to solve the problem and consequently revealed by studies using rats that an azabicyclic compound is eliminated within 24 hours from the rat retina, without exhibiting ocular toxicity, when administered for consecutive days (Non-Patent Literature 6). Therefore, the present inventor had planned to treat malignant tumor by administering the azabicyclic compound to humans for consecutive days. However, in actuality, the compound caused a side effect for vision impairment in the phase I clinical trial. Accordingly, as a result of conducting further studies, the present inventor has found that a specific method of administering an azabicyclic compound represented by the formula (I) described below or a salt thereof can treat malignant tumor with high effectiveness without causing severe eye disorder.

Specifically, the present invention provides the following inventions [1] to [39].

[1] A method for treating malignant tumor, comprising administering an effective amount of 3-ethyl-4-[3-(1-methylethyl)-4-[4-(1-methyl-1H-pyrazol-4-yl)-1H-imidazol-1-yl]-1H-pyrazolo[3,4-b]pyridin-1-yl]benzamide (compound 1) or a salt thereof to a patient in need thereof according to a dosing regimen, wherein the dosing regimen comprises administering the compound 1 or the salt thereof at a dose from 40 mg/body/day to 240 mg/body/day in terms of the amount of the compound 1 for consecutive days, and then providing a withdrawal period of at least 2 days.

[2] The method according to [1], wherein the withdrawal period is from 2 to 3 days.

[3] The method according to [1], wherein the withdrawal period is 2 days.

[4] The method according to any one of [1] to [3], wherein the compound 1 or the salt thereof is administered for 3 to 8 consecutive days.

[5] The method according to any one of [1] to [3], wherein the compound 1 or the salt thereof is administered for 4 to 7 consecutive days.

[6] The method according to any one of [1] to [3], wherein the compound 1 or the salt thereof is administered for 5 consecutive days.

[7] The method according to any one of [1] to [6], wherein the dose of the compound 1 or the salt thereof is from 80 mg/body/day to 200 mg/body/day.

[8] The method according to any one of [1] to [6], wherein the dose of the compound 1 or the salt thereof is from 120 mg/body/day to 160 mg/body/day.

[9] The method according to any one of [1] to [6], wherein the dose of the compound 1 or the salt thereof is 160 mg/body/day.

[10] The method according to any one of [1] to [9], wherein the malignant tumor is gastrointestinal stromal tumor, leukemia, breast cancer, lung cancer, stomach cancer, prostate cancer, ovary cancer and/or large intestinal cancer.

[11] The method according to any one of [1] to [9], wherein the malignant tumor is gastrointestinal stromal tumor, breast cancer and/or lung cancer.

[12] The method according to any one of [1] to [9], wherein the malignant tumor is gastrointestinal stromal tumor.

[13] The method according to any one of [1] to [11], wherein eye disorder is reduced.

[14] A therapeutic agent for malignant tumor, comprising 3-ethyl-4-[3-(1-methylethyl)-4-[4-(1-methyl-1H-pyrazol-4-yl)-1H-imidazol-1-yl]-1H-pyrazolo[3,4-b]pyridin-1-yl]benzamide (compound 1) or a salt thereof, wherein
the compound 1 or the salt thereof is administered according to a dosing regimen comprising administering the compound 1 or the salt thereof at a dose from 40 mg/body/day to 240 mg/body/day in terms of the amount of the compound 1 for consecutive days, and then providing a withdrawal period of at least 2 days.

[15] The therapeutic agent according to [14], wherein the withdrawal period is from 2 to 3 days.

[16] The therapeutic agent according to [14], wherein the withdrawal period is 2 days.

[17] The therapeutic agent according to any one of [14] to [16], wherein the compound 1 or the salt thereof is administered for 3 to 8 consecutive days.

[18] The therapeutic agent according to any one of [14] to [16], wherein the compound 1 or the salt thereof is administered for 4 to 7 consecutive days.

[19] The therapeutic agent according to any one of [14] to [16], wherein the compound 1 or the salt thereof is administered for 5 consecutive days.

[20] The therapeutic agent according to any one of [14] to [19], wherein the dose of the compound 1 or the salt thereof is from 80 mg/body/day to 200 mg/body/day.

[21] The therapeutic agent according to any one of [14] to [19], wherein the dose of the compound 1 or the salt thereof is from 120 mg/body/day to 160 mg/body/day.

[22] The therapeutic agent according to any one of [14] to [19], wherein the dose of the compound 1 or the salt thereof is 160 mg/body/day.

[23] The therapeutic agent according to any one of [14] to [22], wherein the malignant tumor is gastrointestinal stromal tumor, leukemia, breast cancer, lung cancer, stomach cancer, prostate cancer, ovary cancer and/or large intestinal cancer.

[24] The therapeutic agent according to any one of [14] to [22], wherein the malignant tumor is gastrointestinal stromal tumor, breast cancer and/or lung cancer.

[25] The therapeutic agent according to any one of [14] to [22], wherein the malignant tumor is gastrointestinal stromal tumor.

[26] The therapeutic agent according to any one of [14] to [25], wherein eye disorder is reduced.

[27] Use of 3-ethyl-4-[3-(1-methylethyl)-4-[4-(1-methyl-1H-pyrazol-4-yl)-1H-imidazol-1-yl]-1H-pyrazolo[3,4-b]pyridin-1-yl]benzamide (compound 1) or a salt thereof for producing a therapeutic agent for malignant tumor, wherein
the compound 1 or the salt thereof is administered according to a dosing regimen comprising administering the compound 1 or the salt thereof at a dose from 40 mg/body/day to 240 mg/body/day in terms of the amount of the compound 1 for consecutive days, and then providing a withdrawal period of at least 2 days.

[28] The use according to [27], wherein the withdrawal period is from 2 to 3 days.

[29] The use according to [27], wherein the withdrawal period is 2 days.

[30] The use according to any one of [27] to [29], wherein the compound 1 or the salt thereof is administered for 3 to 8 consecutive days.

[31] The use according to any one of [27] to [29], wherein the compound 1 or the salt thereof is administered for 4 to 7 consecutive days.

[32] The use according to any one of [27] to [29], wherein the compound 1 or the salt thereof is administered for 5 consecutive days.

[33] The use according to any one of [27] to [32], wherein the dose of the compound 1 or the salt thereof is from 80 mg/body/day to 200 mg/body/day.

[34] The use according to any one of [27] to [32], wherein the dose of the compound 1 or the salt thereof is from 120 mg/body/day to 160 mg/body/day.

[35] The use according to any one of [27] to [32], wherein the dose of the compound 1 or the salt thereof is 160 mg/body/day.

[36] The use according to any one of [27] to [35], wherein the malignant tumor is gastrointestinal stromal tumor, leukemia, breast cancer, lung cancer, stomach cancer, prostate cancer, ovary cancer and/or large intestinal cancer.

[37] The use according to any one of [27] to [35], wherein the malignant tumor is gastrointestinal stromal tumor, breast cancer and/or lung cancer.

[38] The use according to any one of [27] to [35], wherein the malignant tumor is gastrointestinal stromal tumor.

[39] The use according to any one of [27] to [38], wherein eye disorder is reduced.

Effects of the Invention

The method of the present invention is capable of treating malignant tumor by exerting an excellent antitumor effect while reducing eye disorder.

DETAILED DESCRIPTION OF THE INVENTION

Figure 1:
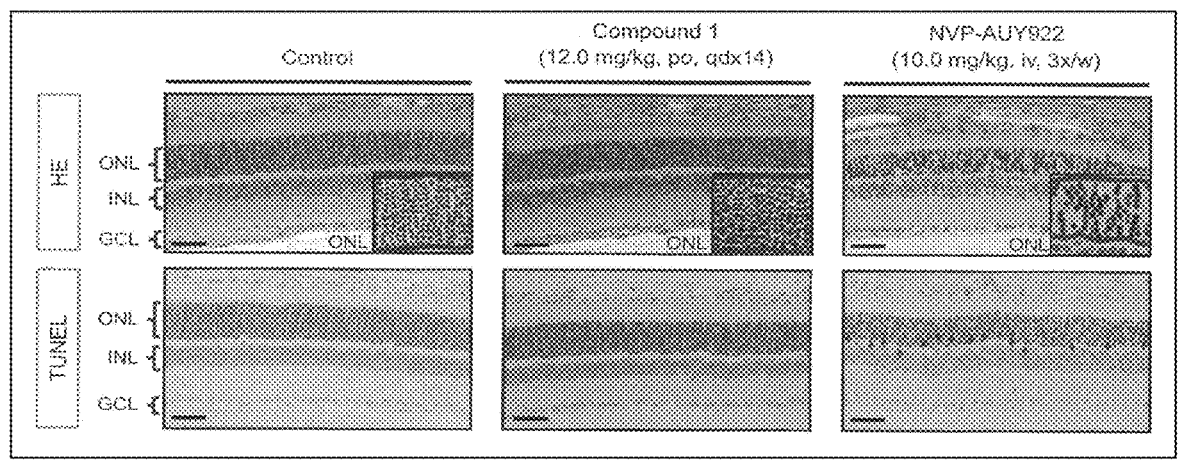
FIG. 1 is a diagram showing results of a histopathological test on compound 1 and NVP-AUY992 in rat eye tissues.

3-Ethyl-4-[3-(1-methylethyl)-4-[4-(1-methyl-1H-pyrazol-4-yl)-1H-imidazol-1-yl]-1H-pyrazolo[3,4-b]pyridin-1-yl]benzamide (hereinafter, also referred to as "compound 1") of the present invention is represented by the following structural formula (I):

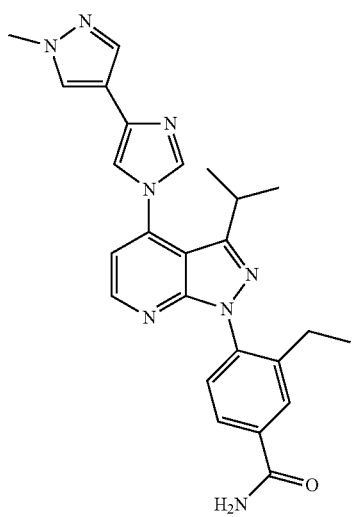

(I)

The compound 1 or a salt thereof is a known compound and can be synthesized in accordance with a method described in, for example, Patent Literature 1 (International Publication No. WO 2011/004610).

The salt of the compound 1 is not particularly limited as long as the salt is pharmaceutically acceptable. Examples thereof include acid-addition salts with inorganic acids such as hydrochloric acid, hydrobromic acid, hydroiodic acid, sulfuric acid, nitric acid, and phosphoric acid, or organic acids such as formic acid, acetic acid, propionic acid, oxalic acid, malonic acid, succinic acid, fumaric acid, maleic acid, lactic acid, malic acid, citric acid, tartaric acid, carbonic acid, picric acid, methanesulfonic acid, p-toluenesulfonic acid, and glutamic acid, salts with inorganic bases such as sodium, potassium, magnesium, calcium, and aluminum, organic bases such as methylamine, ethylamine, meglumine, and ethanolamine, or basic amino acids such as lysine, arginine, and ornithine, and ammonium salts.

The compound 1 also encompasses hydrates, various solvates and crystal polymorphs.

In the present invention, the compound 1 or the salt thereof is administered in its effective amount to a patient in need of treatment of malignant tumor according to a dosing regimen.

In the present invention, the "effective amount" refers to a dose at which the compound 1 or the salt thereof to be administered exhibits an efficacy.

In the present invention, the dose of the compound 1 or the salt thereof per human per day on an administration day is from 40 mg/body/day to 240 mg/body/day in terms of the amount of the compound 1, or this dose is more preferably from 80 mg/body/day to 200 mg/body/day, further preferably from 120 mg/body/day to 160 mg/body/day, most preferably 160 mg/body/day. This dose may be administered in divided portions in one day.

In the present invention, the compound 1 or the salt thereof is administered according to a dosing regimen comprising administering the compound 1 or the salt thereof at the dose for consecutive days, and then providing a withdrawal period for which the compound 1 or the salt thereof is not administered to the patient for at least 2 days. In rats, the plasma concentration and retinal concentration of the compound 1 make a parallel transition. Therefore, as shown in Examples mentioned below, a withdrawal period (plasma concentration decreases to 5% or less of the highest plasma concentration in the duration of administration) of a period for which the plasma concentration of the compound 1 decreases drastically, i.e., at least 2 days, is provided during each administration for consecutive days. This withdrawal period is expected to remove the compound 1 from the retina. Therefore, the dosing regimen is expected to reduce eye disorder caused by the compound 1 or the salt thereof.

The withdrawal period is preferably from 2 to 3 days, particularly preferably 2 days.

The compound 1 or the salt thereof is preferably administered for 3 to 8 consecutive days, more preferably for 4 to 7 consecutive days, particularly preferably for 5 consecutive days.

In the present invention, the dosing regimen preferably comprises administering the compound 1 or the salt thereof for 3 to 8 consecutive days, and then providing a withdrawal period from 2 to 3 days, more preferably comprises administering the compound 1 or the salt thereof for 4 to 7 consecutive days, and then providing a withdrawal period from 2 to 3 days, further preferably comprises administering the compound 1 or the salt thereof for 4 consecutive days, and then providing a withdrawal period of 3 days, or administering the compound 1 or the salt thereof for 5 consecutive days, and then providing a withdrawal period of 2 days, and even more preferably comprises administering the compound 1 or the salt thereof for 5 consecutive days, and then providing a withdrawal period of 2 days. The cycle of this dosing regimen is preferably repeated as many times as possible.

In the present invention, the compound 1 or the salt thereof is most preferably administered according to a dosing regimen comprising administering the compound 1 or the salt thereof at 160 mg/body/day as a dose per human per day on an administration day for 5 consecutive days, and then providing a withdrawal period of 2 days.

In the present invention, specific examples of the malignant tumor to be treated include epithelial cancer (respiratory cancer, digestive system cancer, genitourinary cancer, secretory system cancer, skin cancer, etc.), mesothelioma, breast cancer, sarcoma, hematopoietic organ tumor, central nervous system tumor, and peripheral nervous system tumor. Among them, sarcoma is preferred.

Examples of the respiratory cancer include lung cancer (non-small cell lung cancer, small-cell lung cancer, etc.). Examples of the digestive system cancer include esophageal cancer, stomach cancer, duodenal cancer, liver cancer, biliary tract cancer (gallbladder cancer and bile duct cancer, etc.), pancreatic cancer, large intestinal cancer, and colorectal cancer (colon cancer, rectum cancer, etc.). Examples of the genitourinary cancer include ovary cancer, uterine cancer (uterine cervical cancer, uterine body cancer, etc.), kidney cancer, bladder cancer, prostate cancer, and testicular tumor. Examples of the secretory system cancer include neuroendocrine tumor. Examples of the mesothelioma include pleural mesothelioma, peritoneal mesothelioma, pericardial mesothelioma, and testicular mesothelioma. Examples of the sarcoma include gastrointestinal stromal tumor, bone tumor, and soft tissue tumor. Examples of the hematopoietic organ tumor include leukemia, malignant lymphoma, and multiple myeloma. Examples of the central nervous system tumor include brain tumor. Examples of the peripheral nervous system tumor include malignant neurilemmoma. Among them, gastrointestinal stromal tumor, leukemia, breast cancer, lung cancer, stomach cancer, prostate cancer, ovary cancer and large intestinal cancer are preferred. The lung cancer is preferably non-small cell lung cancer. Among them, leukemia, gastrointestinal stromal tumor, breast cancer and lung cancer are particularly preferred, and gastrointestinal stromal tumor is most preferred.

The "treatment" of malignant tumor of the present invention encompasses postoperative adjuvant chemotherapy which is performed for the prevention of recurrence after surgical extirpation of tumor, and preoperative adjuvant chemotherapy which is performed beforehand for surgical extirpation of tumor.

For pharmaceutical use of the compound 1 or the salt thereof, various dosage forms may be adopted according to therapeutic purposes. Examples of the form can include oral agents (tablets, coated tablets, powders, granules, capsules, solutions, etc.), injections, suppositories, patches, and ointments. An oral agent is preferred for the compound 1 or the salt thereof. These preparations can be formulated by common formation methods usually known in the art using a pharmaceutically acceptable carrier or the like.

Examples of the pharmaceutically acceptable carrier can include various additives generally used in usual drugs, for example, excipients, binders, disintegrants, lubricants, diluents, solubilizers, suspending agents, tonicity agents, pH adjusters, buffers, stabilizers, colorants, flavoring agents, and odor improving agents.

The preparation of the present invention comprising the compound 1 or the salt thereof may be a kit preparation comprising an instruction stating that the compound 1 or the salt thereof is administered according to a dosing regimen comprising administering the compound 1 or the salt thereof at a dose from 40 mg/body/day to 240 mg/body/day for consecutive days, and then providing a withdrawal period of at least 2 days. Specific examples of the "instruction" include package inserts and pamphlets. The kit preparation comprising the instruction may be a kit preparation comprising the instruction printed on or attached to a package, or may be a kit preparation comprising the instruction enclosed together with the compound 1 or the salt thereof in a package.

EXAMPLES

Hereinafter, the present invention will be described in more detail with reference to Examples. However, the present invention is not limited by these Examples by any means. Various changes or modifications can be made by a person ordinarily skilled in the art without departing from the technical belief of the present invention.

Example 1

Purpose: This study was conducted for the purpose of determining a maximum tolerated dose (MTD) and estimating a recommended dose (RD) and an administration method when compound 1 was administered with one cycle set to 21 days targeting solid cancer patients, and of evaluating safety and observing an antitumor effect when the compound 1 was administered with one cycle set to 21 days targeting the patients, for example.

Method: The compound 1 was repeatedly administered between meals once a day in Step 1, and orally administered between meals every other day in Step 2. In Step 1, the initial dose was set to 4.8 mg/m$^2$ (level 1), and the dose of the compound 1 at each level was determined depending on a body surface area. The initial dose of Step 2 (level 1 of Step 2) was set to MTD (mg/m$^2$/day) of Step 1. The study was continued until the disease progressed or an intolerable adverse event occurred.

The dose (mg/body) to a study subject was calculated as described below.

$$\text{Dose } (mg/\text{body}) = \text{Dose } (mg/m^2) \times \text{Body surface area } (m^2)$$

The body surface area (BSA) was calculated to the second decimal place by rounding a value off to two decimal places using the formula of DuBois given below. The dose (mg/body) was calculated to an integer by rounding a value off to the closest whole number, and less than 2 mg was cut off because the minimum tablet dose in this study was 2 mg.

$$BSA = ([\text{Body weight } (kg)]0.425 \times [\text{Body height } (cm)] 0.725) \times 0.007184$$

After determination of MTD, if the body surface area exhibited no relation to a pharmacokinetic parameter according to results of PK, the dose of an additional study after the determination of MTD was set to a fixed dose (mg/body) calculated with BSA as 1.62 m$^2$.

After determination of MTD for once-daily administration, administration was performed by once-daily administration, by alternate-day administration (repeated administration at cycles each involving one-day administration and one-day withdrawal period on the next day), or by a schedule involving administration for 5 consecutive days and 2-day withdrawal period, and evaluation was conducted.

An antitumor effect on tumor was determined according to RECIST Guideline Version 1.1 (European Journal of Cancer 45 (2009) 228-247), and tumor shrinkage was evaluated by comprehensive evaluation on target lesions (lesions equal to or larger than a measurable size depending on a slice width in a diagnosis method (MRI, CT, X ray, etc.) measured at the time of enrollment) and non-target lesions (all lesions except for the target lesions).

Evaluation of Target Lesion

Target lesions were evaluated according to the following 5 levels.

Complete Response (CR):

All non-lymph node target lesions disappeared, and the short axes of all lymph-node target lesions decreased to less than 10 mm (when lymph-node target lesions are selected before treatment, the target lesions may be evaluated as CR even if their sum axis is not 0 mm).

Partial Response (PR):

The sum axis of target lesions decreased by 30% or more as compared with the sum before treatment.

Stable Disease (SD):

Neither tumor shrinkage corresponding to CR or PR nor enlargement corresponding to PD was found.

Progressive Disease (PD):

The sum axis of target lesions increased by 20% or more as compared with the previous smallest sum axis (including the sum before treatment), and the absolute value increased by 5 mm or more.

Not Evaluable (NE):

Examination could not be performed for some reason, and all lesions or some lesions failed to be evaluated, or target lesions could not be evaluated as any of CR, PR, SD, and PD.

Even when the axis of a target lesion was determined to be "too small to measure" (e.g., 2 mm) or was less than 5 mm, an actual measurement value was recorded as much as possible. However, when a lesion was determined to no longer exist, the axis was recorded as 0 mm; and when a lesion was determined to remain, the axis was regarded as 5 mm.

Evaluation of Non-Target Lesion

Non-target lesions were evaluated according to the following 4 levels.

Complete Response (CR):

All non-lymph node non-target lesions disappeared, the short axes of all non-target lesions among lymph-node lesions decreased to less than 10 mm, and the levels of all tumor markers reached equal to or less than the institutional upper normal limits.

Non-CR/Non-PD:

One or more non-lymph node non-target lesions did not disappear, or the short axes of one or more lymph-node non-target lesions reached 10 mm or more, or the level of any of tumor markers exceeded the institutional upper normal limits.

Progressive Disease (PD):

Evident Exacerbation of an Existing Non-Target Lesion

The "evident exacerbation" in the presence of a target lesion means that it is determined that treatment should be stopped due to increase in overall tumor mass even if an effect on the target lesion is SD or PR. Slight "exacerbation" based on a tumor mass does not correspond to the "evident exacerbation". The evident exacerbation in the absence of a target lesion means, for example, increase in tumor mass corresponding to the enlargement of 73% of a tumor volume (which is equal to the enlargement of 20% of the axis of a measurable lesion).

Not Evaluable (NE):

Examination could not be performed for some reason, and all lesions or some lesions failed to be evaluated, or non-target lesions could not be evaluated as any of CR, Non-CR/non-PD, and PD. However, even taken into account that the lesions which were not evaluated, if it was logically evident that any evaluated effect will not be changed, such a case was not counted as NE.

Evaluation of Best Overall Response

The overall response of each case was evaluated according to the following criteria, and the best overall response was evaluated after confirmation of duration of the effect.

TABLE 1

Evaluation of overall response (in presence of target lesion)

| Overall response | Target lesion | Non-target lesion | New lesion |
|---|---|---|---|
| CR | CR | CR | Absent |
| PR | CR | Non-CR/non-PD | Absent |
| PR | CR | NE | Absent |
| PR | PR | Other than PD or NE | Absent |

TABLE 1-continued

| | | | |
|---|---|---|---|
| SD | SD | Other than PD or NE | Absent |
| NE | NE | Other than PD | Absent |
| PD | PD | Any level | Absent or Present |
| PD | Any level | PD | Absent or Present |
| PD | Any level | Any level | Present |

Evaluation of overall response (in absence of target lesion)

| Overall response | Non-target lesion | New lesion |
|---|---|---|
| CR | CR | Absent |
| Non-CR/non-PD | Non-CR/non-PD | Absent |
| NE | NE | Absent |
| PD | PD | Absent or Present |
| PD | Any level | Present |

The best overall response was evaluated according to the following 5 levels.

CR: After reaching CR first, the CR status was maintained in examination performed after a lapse of at least 4 weeks or longer.

PR: After reaching PR first, the PR status was maintained in examination performed after a lapse of at least 4 weeks or longer.

SD: Neither CR nor PR was attained and no PD was confirmed in examination performed after a lapse of at least 6 weeks or longer from the start of administration.

PD: PD of target lesions or non-target lesions was confirmed without satisfying the criterion of CR, PR and SD, or the appearance of a new lesion was confirmed.

If any of target lesions, non-target lesions, and the presence or absence of the appearance of new lesions were not evaluable, such a case was counted as NE.

Response Rate (RR)

Proportion of cases with best overall response of CR and PR in an analyte population.

Disease Control Rate (DCR)

Proportion of cases with best overall response of CR, PR, Non-CR/non-PD, or SD continued for 12 weeks or longer in an analyte population.

In this test, ophthalmologic examination was conducted in order to evaluate eye disorder.

The ophthalmologic examination was carried out before enrollment, in the duration of administration, and during follow-up. In the duration of administration, ophthalmologic interview, visual acuity examination (corrected), intraocular pressure examination, fundus examination, slit-lamp microscopy, optical coherence tomography (OCT), and color perception examination were carried out for 21 days±1 day from the start of administration. Observation and examination before enrollment were carried out as immediately before the enrollment as possible. In addition to the determined ophthalmologic examination described above, ophthalmologic examination was appropriately carried out when eye problems were found by regular interview by clinical investigators or by declaration from patients themselves.

The grading of the severity of adverse events which occurred in the eyes was evaluated according to the criteria of Common Terminology Criteria for Adverse Events (CTCAE Ver. 4.03) (Table 2).

TABLE 2

| CTCAE v4.0 term | Grade 1 | Grade 2 | Grade 3 | Grade 4 |
|---|---|---|---|---|
| Eye disorder | Asymptomatic or mild symptoms; clinical or | Moderate; minimal, local or noninvasive | Severe or medically significant but not | Sight-threatening consequences; urgent |

TABLE 2-continued

| CTCAE v4.0 term | Grade 1 | Grade 2 | Grade 3 | Grade 4 |
|---|---|---|---|---|
| | diagnostic observations only; intervention not indicated | intervention indicated; limiting age-appropriate instrumental ADL | immediately life-threatening; hospitalization or prolongation of hospitalization indicated; disabling; limiting self care ADL | intervention indicated; best corrected visual acuity or worse in the affected eye (0.1 or less) |

Table 3 shows results of evaluating an antitumor effect on the tumors described above. Patients with non-small cell lung cancer, gastrointestinal stromal tumor, thymic cancer, biliary tract cancer, breast cancer, adenoid cystic cancer, pancreatic cancer, stomach cancer, ovary cancer, skin cancer, neuroblastoma, head and neck cancer, esophageal cancer, kidney cancer, colorectal cancer, sarcoma, mesothelioma, or the like entered the test.

As a result of the study described above, MTD was 107.5 mg/m$^2$/day for administration for consecutive days and 210 mg/m$^2$/day for alternate-day administration.

The comparison of doses based on body surface areas with actual doses showed little influence on the correlation between the doses and the area under the plasma concentration-time curve (AUC) even if a method of calculating doses differed. Therefore, MTD was converted to the fixed dose (160 mg/body/day for administration for consecutive days and 340 mg/body/day for alternate-day administration), and an additional study was conducted.

Table 4 shows results of evaluating eye disorder in a consecutive-day administration group, an alternate-day administration group and a group given administration for 5 consecutive days and 2-day withdrawal period.

TABLE 4

Results about eye disorder related to treatment

| | | | | | QD (consecutive-day administration) Step 1 Dose escalation | | | | | | QD × 5 (5-day administration 2-day drug holiday) Step 1 | | |
|---|---|---|---|---|---|---|---|---|---|---|---|---|---|
| | Total n = 61 | | | Lv. 1 to 5 (4.8-76.8 mg/m$^2$) n = 7 | | | Lv. 6 (107.5 mg/m$^2$) n = 6 | | | Lv. 7 (150.5 mg/m$^2$) n = 3 | | Expansion (160 mg/body) n = 19 | |
| Adverse event, n (%) | G1 | G2 | ≥G3 | G1 | G2 | ≥G3 | G1 | G2 | ≥G3 | G1 | G2 | ≥G3 | G1 | G2 | ≥G3 |
| Eye Disorder | 14 (23.0) | 4 (6.6) | 2 (3.3) | 1 (14.3) | | | 3 (50.0) | 2 (33.3) | | | 2 (66.7) | | 5 (26.3) | | |

| | | QOD (alternate-day administration) Step 2 Dose escalation | | | | | | | QOD (alternate-day administration) Step 2 Expansion (340 mg/body) n = 6 | | |
|---|---|---|---|---|---|---|---|---|---|---|---|---|
| | | Lv. 1 to 2 (107.5-150.5 mg/m$^2$) n = 9 | | | Lv. 3 (210.7 mg/m$^2$) n = 6 | | | Lv. 4 (295.0 mg/m$^2$) n = 5 | | | | |
| Adverse event, n (%) | | G1 | G2 | ≥G3 | G1 | G2 | ≥G3 | G1 | G2 | ≥G3 | G1 | G2 | ≥G3 |
| Eye disorder | | 2 (22.2) | | | 1 (16.7) | | | 1 (16.7) | | | 3 (60.0) | 1 (20.0) | |

Abbreviations,
G: grade,
Lv: level

TABLE 3

Results of tumor response in solid cancer based on RECIST Guideline Version 1.1 for protocol set

| | QD n = 16 (%) | QD × 5 n = 18 (%) | QOD n = 26 (%) |
|---|---|---|---|
| PR | 2 (12.5) | 0 (0.0) | 1 (3.8) |
| SD | 7 (43.8) | 9 (50.0) | 9 (34.6) |
| PD | 5 (31.3) | 8 (44.4) | 15 (57.7) |
| NE | 2 (12.5) | 1 (5.6) | 1 (3.8) |
| RR | 2 (12.5) | 0 (0.0) | 1 (3.8) |
| DCR (≥12 weeks) | 5 (31.3) | 7 (38.9) | 4 (14.4) |

The degree of eye disorder at MTD in the group given administration for 5 consecutive days and 2-day withdrawal period and the alternate-day administration group was limited to grade 1, unlike the consecutive-day administration group.

This study was registered and conducted as NCT02965885 in ClinicalTrials.gov and JapicCTI-142444 in Japan Pharmaceutical Information Center.

Example 2

Purpose: In order to evaluate the effectiveness and safety, etc. of compound 1, this study was conducted for the purpose of evaluating the effectiveness and safety, etc. of the compound 1, targeting patients with local progressive unresectable or metastatic GIST who received the administration of imatinib, sunitinib or regorafenib in the past.

From the results of the study of Example 1, this study was carried out according to a schedule involving administration for 5 consecutive days and 2-day withdrawal period. The daily dose of the compound 1 was 160 mg/body/day for oral administration. One cycle was set to 21 days. The administration of the compound 1 was continued until the end date of the clinical trial or any of predetermined criterion for discontinuation were applicable.

For the evaluation of an antitumor effect, CT scan was carried out before the start of administration, every 3 weeks for subsequent 6 weeks, every 6 weeks for subsequent 3 months, and then every 8 weeks until the end of the test. Progression-free survival (PFS) stipulated by RECIST Guideline Version 1.1 was evaluated.

Median PFS brought about by the compound 1 was 4.4 months. This result was favorable even when compared with the median PFS of 4.8 month in a group given the administration of regorafenib, a drug for the third-line treatment of progressive or unresectable GIST, or the median PFS of 0.9 months in a placebo administration group. The compound 1 also exhibited good tolerability. Although digestive tract disorder and elevated plasma creatinine levels were observed as related adverse events, all of these adverse events related to treatment were found to be reversible by the discontinuation of administration or decrease in dose and therefore considered to be controllable.

For the evaluation of eye disorder, interview, visual acuity examination (corrected), intraocular pressure measurement, fundus examination, slit-lamp microscopy, optical coherence tomography (OCT), and color perception examination were carried out at the time of a baseline within 14 days before enrollment and at the completion of administration of the study drug.

Interview, visual acuity examination (corrected), intraocular pressure measurement, fundus examination, optical coherence tomography (OCT), slit-lamp microscopy, and color perception examination were further carried out as much as possible every 12 weeks after the start of administration of the study drug and every 24 weeks on week 48 or later (within ±7 days).

In addition to the determined ophthalmologic examination described above, ophthalmologic examination was appropriately carried out when eye problems were found by regular interview by clinical investigators or by declaration from patients themselves.

The frequency of occurrence of eye disorder was 20%, and eye disorder in all the patients was at grade 1. This indicated the contribution of the dosing regimen of this test. These results suggested that the dosing regimen of administration for 5 consecutive days and 2-day withdrawal period is a suitable dosing regimen which exhibits an antitumor effect while reducing eye disorder.

This study was registered and conducted as JapicCTI-163182 in Japan Pharmaceutical Information Center.

Reference Example 1

Evaluation of Tissue Distribution Profile and Ocular Toxicity of Compound 1 in Rat—(1):
Histopathological Study in Rat Eye Tissue Method: Compound 1 was orally administered at 12 mg/kg/day to 6-week-old male Sprague-Dawley (SD) rats (Charles River Laboratories Japan, Inc., Japan) every day for 2 weeks. NVP-AUY922 (available from Funakoshi Co., Ltd., Japan) adjusted to 5% (v/v) dimethyl sulfoxide and 50 (v/v) Tween 20 in saline was intravenously administered at 10.0 mg/kg/day to SD rats three times a week for 2 weeks. The eyes were collected 24 hours after the final dose, fixed in a Davidson's solution over 48 hours, and preserved in a 10% (v/v) buffered formalin solution before predetermined paraffine embedding and slicing. The eye slices were stained with hematoxylin and eosin, followed by terminal deoxynucleotidyl transferase dUTP nick end labeling (TUNEL: ApopTagPlus Peroxidase In Situ Apoptosis Detection Kit, Merck-Millipore).

Results: The results are shown in FIG. 1. As is evident from these results, NVP-AUY922, another HSP90 inhibitor, was found to cause marked degeneration and disarrangement in the outer nuclear layer of the retina and to considerably increase the number of TUNEL-positive apoptotic cells ascribable to the retinal distribution of NVP-AUY922. On the other hand, the compound 1 did not cause any histopathological change in the outer nuclear layer of the retina, and such elevation of the number of apoptotic cells was not observed.

Reference Example 2

Evaluation of Tissue Distribution Profile and Ocular Toxicity of Compound 1 in Rat—(2):
Quantification of Plasma, Tumor and Retinal Tissue Exposed to Compound 1 by Oral Administration Method: Compound 1 and NVP-AUY922 were each administered to tumor-bearing F344 nude rats by oral or intravenous administration. After the administration, plasma, the retina, and tumor were collected according to a sampling schedule. The retina or tumor samples were homogenized in phosphate-buffered saline. The plasma and the homogenized samples were analyzed by liquid chromatography-tandem mass spectrometry or high-performance liquid chromatography. The pharmacokinetics of the compound 1 were calculated by use of the non-compartmental analysis method (Methods Mol Biol 2012; 929: 377-89).

Figure 2:
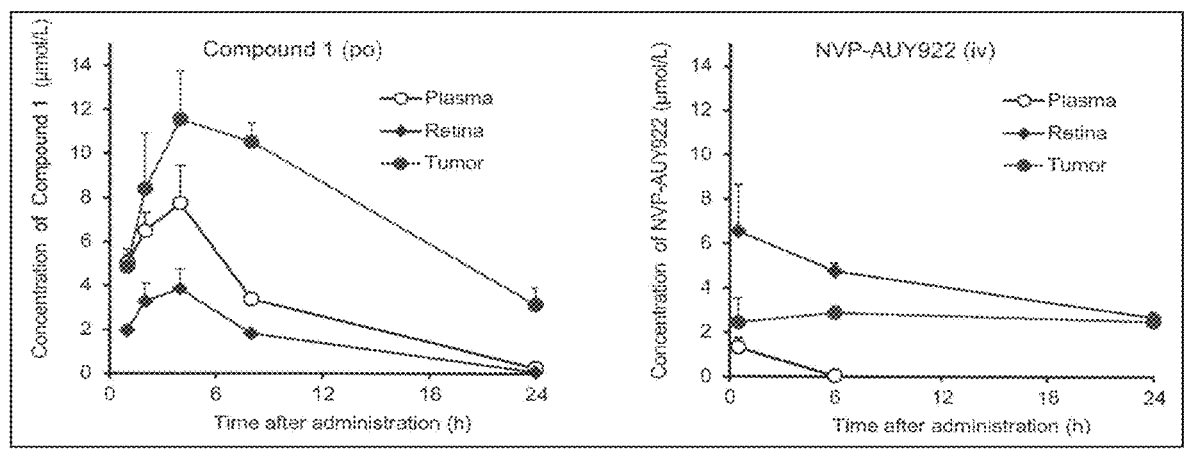
FIG. 2 is a diagram showing quantitative results of plasma, tumor and retinal tissues exposed to compound 1 by oral administration and NVP-AUY992 by intravenous administration.

Results: The results are shown in FIG. 2. From these results, the compound 1 was found to distribute in a larger amount in tumor than in the retina and plasma in tumor-bearing rats. In the tumor-bearing rats, the compound 1 was confirmed to be removed from the retina within 24 hours. On the other hand, NVP-AUY922 distributed in a larger amount in the retina than in plasma and was detected from the retina even 24 hours after administration.

Reference Example 3

Evaluation of Tissue Distribution Profile and Ocular Toxicity of Compound 1 in Rat—(3):
Quantification of Plasma and Retinal Tissue Exposed to Compound 1 by Intravenous Administration Method: Compound 1 was administered to tumor-bearing F344 nude rats by intravenous administration. Plasma and the retina were collected 30 minutes and 6 hours after the administration. The retina samples were homogenized in phosphate-buffered saline. The plasma and the homogenized samples were analyzed by liquid chromatography-tandem mass spectrometry or high-performance liquid chromatography. The pharmacokinetics of the compound 1 were calculated by use of the non-compartmental analysis method (Methods Mol Biol 2012; 929: 377-89).

Figure 3:
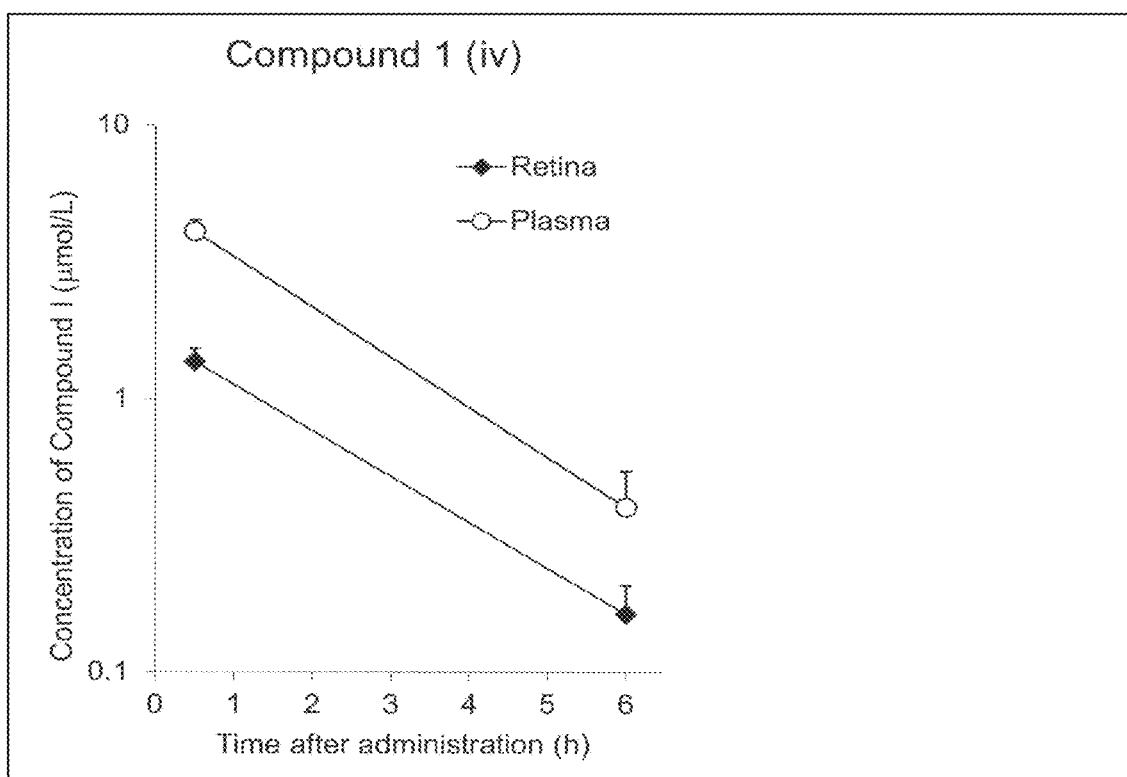
FIG. 3 is a diagram showing quantitative results of plasma and retinal tissues exposed to compound 1 by intravenous administration.

Results: The results are shown in FIG. 3. From these results, the distribution of the compound 1 was lower in the retina than in plasma, demonstrating that the distributions to both tissues show equilibrium transition respectively.

The invention claimed is:
1. A method for treating malignant tumor, comprising administering 3-ethyl-4-[3-(1-methylethyl)-4-[4-(1-methyl-

1H-pyrazol-4-yl)-1H-imidazol-1-yl]-1H-pyrazolo[3,4-b]pyridin-1-yl]benzamide or a salt thereof (compound 1) to a patient in need thereof
    at a dose of from 40 mg/body/day to 240 mg/body/day of compound 1 for at least one day, and then providing a withdrawal period of at least 2 days.

2. The method according to claim 1, wherein the withdrawal period is from 2 to 3 days.

3. The method according to claim 1, wherein the withdrawal period is 2 days.

4. The method of claim 1, wherein compound 1 is administered for 3 to 8 consecutive days.

5. The method of claim 1, wherein compound 1 is administered for 4 to 7 consecutive days.

6. The method of claim 1, wherein the compound 1 is administered for 5 consecutive days.

7. The method of claim 1, wherein the dose of the compound 1 is from 80 mg/body/day to 200 mg/body/day.

8. The method of claim 1, wherein the dose of the compound 1 is from 120 mg/body/day to 160 mg/body/day.

9. The method of claim 1, wherein the dose of the compound 1, is 160 mg/body/day.

10. The method of claim 1, wherein the malignant tumor is gastrointestinal stromal tumor, leukemia, breast cancer, lung cancer, stomach cancer, prostate cancer, ovary cancer and/or large intestinal cancer.

11. The method of claim 1, wherein the malignant tumor is gastrointestinal stromal tumor, breast cancer and/or lung cancer.

12. The method of claim 1, wherein the malignant tumor is gastrointestinal stromal tumor.

13. The method of claim 1, which reduces the severity of eye disorder adverse events as compared to a dosing regimen without at least one withdrawal period during the administration of compound 1.

14. A method of administering 3-ethyl-4-[3-(1-methylethyl)-4-[4-(1-methyl-1H-pyrazol-4-yl)-1H-imidazol-1-yl]-1H-pyrazolo[3,4-b]pyridin-1-yl]benzamide or a salt thereof (compound 1) which reduces adverse eye events when administering compound 1 to a subject with a malignant tumor, which comprises administering
    compound 1 at a dose from 40 mg/body/day to 240 mg/body/day of compound 1 for at least one day, followed a withdrawal period of at least 2 days to reduce adverse eye events.

15. The method of claim 14, wherein the withdrawal period is from 2 to 3 days.

16. The method of claim 14, wherein the withdrawal period is 2 days.

17. The method of claim 14, wherein the compound 1 is administered for 3 to 8 consecutive days.

18. The method of claim 14, wherein the compound 1 is administered for 4 to 7 consecutive days.

19. The method of claim 14, wherein the compound 1 is administered for 5 consecutive days.

20. The method of claim 14, wherein the dose of the compound 1 is from 80 mg/body/day to 200 mg/body/day.

21. The method of claim 14, wherein the dose of the compound 1 is from 120 mg/body/day to 160 mg/body/day.

22. The method of claim 14, wherein the dose of the compound 1 is 160 mg/body/day.

23. The method of claim 14, wherein the malignant tumor is gastrointestinal stromal tumor, leukemia, breast cancer, lung cancer, stomach cancer, prostate cancer, ovary cancer and/or large intestinal cancer.

24. The method of claim 14, wherein the malignant tumor is gastrointestinal stromal tumor, breast cancer and/or lung cancer.

25. The method of claim 14, wherein the malignant tumor is gastrointestinal stromal tumor.

26. The method of claim 14, wherein the severity of eye adverse events is reduced.

* * * * *